United States Patent
Wartman et al.

(10) Patent No.: US 6,871,645 B2
(45) Date of Patent: Mar. 29, 2005

(54) REDUCED-OXYGEN BREATHING DEVICE

(75) Inventors: Richard Wartman, Pensacola, FL (US); Michael Stiney, Pensacola, FL (US); Eric Bower, Pensacola, FL (US); Paul Gardetto, Yorktown, VA (US); Charles Vacchiano, Gulf Breeze, FL (US); Kenneth Sausen, Arlington, TN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/244,003

(22) Filed: Sep. 16, 2002

(65) Prior Publication Data

US 2003/0070678 A1 Apr. 17, 2003

Related U.S. Application Data

(60) Provisional application No. 60/318,827, filed on Sep. 14, 2001.

(51) Int. Cl.$^7$ .............................................. A61M 16/00
(52) U.S. Cl. ........................... 128/203.12; 128/203.25; 128/205.11; 128/204.22; 128/204.29
(58) Field of Search ...................... 128/202.12, 203.25, 128/205.11, 205.25, 205.26, 205.27, 205.28, 204.22, 914, 206.15, 203.12, 204.29

(56) References Cited

U.S. PATENT DOCUMENTS

| | | | | |
|---|---|---|---|---|
| 1,827,530 A | * | 10/1931 | Le Grand ..................... 600/21 |
| 2,373,333 A | * | 4/1945 | St Onge ..................... 165/234 |
| 5,101,819 A | * | 4/1992 | Lane ..................... 128/204.18 |
| 5,207,623 A | * | 5/1993 | Tkatchouk et al. ........... 482/61 |
| 5,799,652 A | * | 9/1998 | Kotliar ................... 128/205.11 |
| 5,850,833 A | * | 12/1998 | Kotliar ................... 128/202.12 |
| 5,860,857 A | * | 1/1999 | Wasastjerna et al. ....... 454/338 |
| 5,924,419 A | * | 7/1999 | Kotliar ................. 128/205.111 |
| 5,988,161 A | * | 11/1999 | Kroll ..................... 128/202.12 |
| 6,009,870 A | * | 1/2000 | Tkatchouk ............. 128/202.12 |
| 6,165,105 A | * | 12/2000 | Boutellier et al. ............ 482/13 |
| 6,561,185 B1 | * | 5/2003 | Kroll ..................... 128/202.12 |
| 6,565,624 B2 | * | 5/2003 | Kutt et al. ....................... 95/8 |

* cited by examiner

Primary Examiner—Henry Bennett
Assistant Examiner—Mital Patel
(74) Attorney, Agent, or Firm—Joseph K. Hemby, Jr.; Philip E. Ketner

(57) ABSTRACT

The present invention includes a non-rebreathing circuit coupled with computer-controlled gas adjustments. Ambient air is diluted with nitrogen on a breath-by-breath basis to provide precise control over the inspired concentration of oxygen/nitrogen mixture, thereby simulating selected altitudes on an almost instantaneous basis. Carbon dioxide and water vapor exhaled by the subject are released into the environment and absorption is not necessary. In addition, the mixed gas can be administered through a standard aviator's oxygen mask, increasing the realism of the simulation and removing obvious external cues on the nature of the experiment. Maintenance on the mixing loop is low when compared to re-breathing units, since no consumable items are necessary to absorb water vapor or carbon dioxide. A mixing device provides a homogenized mixture of nitrogen/oxygen fluid to the subject.

20 Claims, 7 Drawing Sheets

| SEA LEVEL | Torr | ATA | PIO2 | PAO2 | TABLE OF O2 Sat | FIO2 Reqd FOR O' EQUIV | Psup for 8K= | OXYGEN CONTENT | VARIABLES | VALUE |
|---|---|---|---|---|---|---|---|---|---|---|
| 0 | 760 | 1.000 | 159.60 | 103.028 | 97 | 21.00% | | 21.00% | | |
| 5000 | 632 | 0.832 | 132.72 | 76.1475 | 94 | 25.52% | | 17.28% | PACO2= | 39 |
| 10000 | 522 | 0.687 | 109.62 | 53.0475 | 85 | 31.31% | | 14.08% | | |
| 13000 | 465 | 0.612 | 97.65 | 41.0775 | 75 | 35.48% | | 12.43% | RQ= | 0.8 |
| 15000 | 429 | 0.564 | 90.09 | 33.5175 | 62 | 38.74% | | 11.36% | | |
| 18000 | 380 | 0.500 | 79.80 | 23.2275 | 42 | 44.28% | | 9.96% | FIO2= | 0.21 |
| 20000 | 350 | 0.461 | 73.50 | 16.9275 | 28 | 48.53% | | 9.09% | | |
| 22000 | 321 | 0.422 | 67.41 | 10.8375 | 15 | 53.49% | | 8.24% | PH2O= | 47 |
| 25000 | 282 | 0.371 | 59.22 | 2.6475 | 2 | 62.01% | | 7.11% | | |
| 28000 | 247 | 0.325 | 51.87 | -4.7025 | | 72.36% | | 6.09% | | |
| 30000 | 226 | 0.297 | 47.46 | | COLUMN | 80.41% | | 5.43% | | |
| 34000 | 188 | 0.247 | 39.48 | | ONLY | 100.68% | | 4.38% | | |
| 40000 | 141 | 0.186 | 29.61 | | VALID | | 6 | 3.01% | | |
| 43000 | 122 | 0.161 | 25.62 | | for | | 25 | 2.46% | | |
| 45000 | 111 | 0.146 | 23.31 | | FIO2 = | | 36 | 2.14% | | |
| 50000 | 87 | 0.114 | 18.27 | | 0.21 | | 60 | 1.45% | | |
| 55000 | 69 | 0.091 | 14.49 | | | | 78 | 0.92% | | |
| 60000 | 54 | 0.071 | 11.34 | | | | 93 | 0.49% | | |
| 63000 | 47 | 0.062 | 9.87 | | | | 100 | 0.28% | | |

PAO2=FIO2(Pb-PH2O)-PACO2(FIO2+(1-FIO2)/RQ)

FIG. 6

REDUCED-OXYGEN BREATHING DEVICE

CROSS-REFERENCE

This application claims priority under 35 USC 119(e) based on the filing date of its U.S. Provisional Application No. 60/318,827, filed Sep. 14, 2001.

BACKGROUND OF THE INVENTION

1. Field of the Invention

The present invention relates to a method and apparatus for providing air with a less than ambient concentration of oxygen (reduced-oxygen air) to a human or other subject. More particularly, the invention relates to a method and apparatus for inducing hypoxia in a subject by delivering enriched nitrogen (and, thereby, reduced-oxygen) air to the subject in an isobaric setting to simulate various altitudes above sea level over relatively short periods.

2. Description of Prior Art

Altitude sickness strikes thousands of individuals every year resulting in problems from sleep disorders to pulmonary edemas to death. These individuals are pilots, skiers, mountain climbers, or merely business travelers to high altitude regions. The key to dealing with the altitude sickness is taking advantage of the body's ability to gradually acclimatize through a transition through progressively higher altitudes. Unfortunately, most individuals do not have the time to acclimatize.

The physiology of altitude sickness and the adjustment to altitude is covered in numerous textbooks. An excellent one is *"Medicine For Mountaineering"* by James Wilkerson, M.D. Copyright 1992, published by The Mountaineers of Seattle, Wash. from which much of the immediately following discussion is derived.

The body adjusts to altitude by increasing respiratory volume, increasing the pulmonary artery pressure, increasing the cardiac output, increasing the number of red blood cells, increasing the oxygen carrying capability of the red blood cells, and even changing body tissues to promote normal function at lower oxygen levels.

For example, at an altitude level of 3,000 feet the body already begins increasing the depth and rate of respiration. As a result of this, more oxygen is delivered to the lungs. In addition, the pulmonary artery pressure is increased which opens up portions of the lung which are normally not used, thus increasing the capacity of the lungs to absorb oxygen. For the first week or so, the cardiac output increases to increase the level of oxygen delivered to the tissues. The body also begins to increase the production of red blood cells. Other changes include the increase of an enzyme (DPG) which, in-turn, facilitates the release of oxygen from the blood and increase the numbers of capillaries within the muscle to better facilitate the exchange of blood with the muscle.

Tissue hypoxia is caused by the body's inability to obtain or utilize an adequate supply of oxygen. Under normal circumstances, there are three main ways by which this can occur. An individual can breathe a gas mixture in which the percentage of oxygen in the inspired air is insufficient to support adequate cellular respiration. This type of hypoxia (hypoxic hypoxia) can be found in situations where gases such as nitrogen or carbon dioxide are present in higher than normal concentrations relative to air at sea level, thereby displacing oxygen in the gas mixture. Breathing a gas mixture that contains approximately the same percentages of gases as found at sea level, but where the total pressure of the gas mixture is reduced causes a second form of hypoxia (hypobaric hypoxia). This is the situation encountered in altitude exposures. Finally, a third form of hypoxia (histiotoxic hypoxia) is caused by certain toxins (e.g. carbon monoxide, cyanide) that interfere with the body's utilization of oxygen at the cellular level.

Physiologically, the response to each of these types of hypoxia is similar as the organism attempts to compensate for the reduced amount of oxygen available for cellular metabolism. The rate and depth of respiration increases and the heart rate also increases. Subjectively, the individual experiences the sensations of shortness of breath and anxiety. If the hypoxia is severe enough, or if compensatory mechanisms cannot be sustained for any reason, other symptoms become apparent. Organs that have a high oxygen demand are affected first. Cognitive processes are impaired, and the subject may experience marked confusion or ataxia. If the hypoxia persists, coma and death result.

Investigators have utilized different mechanisms to study the effects of hypoxia on human physiology. Exposure to hypobaric environments has been the technique most frequently utilized in aviation settings. The military and commercial aviation industry both spend large sums of money annually training aviators to recognize and experience the signs and symptoms of hypoxia. This type of training is accomplished through the use of hypobaric chambers at fixed sites. These chambers have several drawbacks. Because they are expensive to construct and operate, only a limited number of these chambers can be fielded. Despite their relatively large size, however, they are generally too small to incorporate mission simulators into the hypoxic environment. Additionally, any equipment that is placed into the chamber must be extensively tested to ensure that it is compatible with the reduced barometric pressures within the chamber. Some investigators believe that if hypoxia training and flight could be combined, the face validity of the training scenario would be improved, and the overall training benefit would be significantly increased.

Other investigators have utilized mixed-gas hypoxia (i.e., hypoxic hypoxia) for a variety of reasons, most typically to investigate the physiologic effects of breathing gas mixtures containing a reduced percentage of oxygen, and/or an elevated concentration of carbon dioxide. This technique has several drawbacks. Gas mixtures require the ability to accurately blend and compress gases. Premixed gases also require some storage capacity. Typically, several cylinders of gas mixtures are connected in parallel to a manifold, which is in turn connected to the experimental subject. By changing valve settings on the manifold, differing gas mixtures can be administered. Concentrations are, therefore, limited to only those mixtures created before the experiment. Since the gas mixtures are discrete, no intermediate concentrations can be achieved. The gas mixtures can be administered through a conventional breathing apparatus, but the dependence on cylinders of premixed gases outweighs this convenience. However, because these devices also provoke the symptoms of hypoxia, one potentially useful avenue for these devices could be in the simulation of altitude exposure. Experiments have shown that the physical symptoms and performance deficits induced by hypobaric and mixed-gas hypoxia are qualitatively similar.

Certain devices like the present invention have been presented in the literature as being of two fundamental types. The simplest type exhibits a relatively large volume, closed breathing circuit. An experimental subject is connected to the circuit, and breathes off the reservoir, gradually exchanging the gas mixture present in the reservoir with his or her own exhaled gas (re-breathing). Carbon monoxide and water vapor from the subject may or may not be removed from the reservoir, depending on the experimental design. This type of device is limited in several important respects. The rate at which the oxygen in the reservoir is depleted is dependent on the ratio of the subject's minute ventilation volume and the volume of the reservoir. Since this device has no means to replace oxygen in the reservoir, this device cannot maintain a gas mixture at a particular ratio or concentration. The duration of the experiment is therefore limited to the time it takes for oxygen levels in the reservoir to fall to critical levels. Additionally, the concentration of oxygen in the system is constantly changing making interpretation of the results much more challenging.

A more advanced type of re-breathing circuit has been developed that addresses some of the shortcomings of the simple re-breathing loop. In this device, the subject exhales into a mixing loop, and an oxygen sensor monitors the concentration of oxygen in the loop. Computer software compares the actual concentration of oxygen to the expected concentration of oxygen, and oxygen is added to the mixing loop to hold the concentration of oxygen at a preset level. A shortcoming of this system is that carbon dioxide and water vapor must be continuously removed. Volume loss through the absorption of water vapor and carbon dioxide forces the addition of a replacement volume of gas (typically nitrogen) into the circuit. Because this is a re-breathing apparatus, special masks are required for the subject. Masks are connected to the re-breathing loop by two flexible hoses. Because of the weight of the one-way valve system required, and the weight of the hoses, this apparatus is cumbersome to the subject, and is not well suited for operation in small or confined spaces.

Examples of some of these and similar devices are as follows: Gamow (U.S. Pat. No. 5,398,678) discloses a portable chamber to simulate higher altitude conditions by increasing the pressure within the chamber above that of the ambient pressure, whereas the present invention is practiced in isobaric conditions; Lane (U.S. Pat. No. 5,101,819) teaches a method of introducing nitrogen into a flight training hypobaric chamber (not as in the isobaric conditions of the present invention) to simulate the lower oxygen concentrations at higher altitudes for fighter pilots; Kroll (U.S. Pat. No. 5,988,161) teaches a portable re-breathing device using increasing levels of carbon dioxide to displace oxygen and used to acclimate individuals to higher altitudes, whereas the present invention does not employ this use of exhaled gases (re-breathing) to displace the oxygen; Koni, et al. (U.S. Pat. No. 4,345,612) discloses an apparatus for delivery of a regulated flow of anesthetic gases but uses flow rate input data (not direct measurement of the mixed gases as in the present invention) to control release of gases and is not designed to allow for dynamic conditions; Lampotang, et al. (U.S. Pat. No. 6,131,571) also teaches a device for delivery of anesthetic gases but is more concerned with improved mixing of the gases and maintenance of proper pressure (operating as a ventilator) and is fundamentally different from the present invention, again, in both application and operation (pressure differentials, not direct measurement of mixed gases, is the means for computer control and is utilized to maintain proper system volume, not gas concentrations as in the present invention); and, finally, Marshall, et al. (U.S. Pat. No. 6,196,051) teaches an apparatus for determining odor levels in gas streams but utilizes a mass flow sensor at the inlet valve to regulate the flow of gases into the mixing chamber (not by direct measurement of chamber gases as in the present invention).

SUMMARY OF THE INVENTION

The present invention addresses the shortcomings in the prior art by using a non-rebreathing circuit coupled with computer-controlled gas adjustments. Ambient air is diluted with nitrogen on a breath-by-breath basis, providing the experimenter with precise control over the inspired concentration of oxygen on an almost instantaneous basis. Carbon dioxide and water vapor are exhaled by the subject are released into the environment, absorption is not necessary. The small size of the present invention makes fitting the device into cramped simulator environments possible, and multiple units may be incorporated into multi-place aircraft simulators. Maintenance of the mixing loop is low when compared to re-breathing units, since no consumable items are necessary to absorb water vapor and/or carbon dioxide.

The Reduced-Oxygen Breathing Device (ROBD) is designed to create a selected static or dynamic gas mixture for breathing and is intended to induce a state of hypoxia in the subject. The reduced-oxygen breathing apparatus is made up of the following minimum elements: a vessel for gas mixing; an ambient air inlet; an outlet to provide the controlled gas mixture to a subject; an oxygen concentration sensor; a nitrogen gas supply; a nitrogen valve; and a controller for gas mixing, whereby the sensor sends a signal to the controller which manipulates said signal and provides an output signal to the nitrogen valve that adjusts the nitrogen gas supply to the gas mixing vessel in accordance with parameters set by an operator.

Accordingly, an object of this invention is to provide a reduced-oxygen breathing device for providing oxygen-reduced (hypoxic)/nitrogen-enriched air (relative to ambient conditions) to a subject.

Another object of the invention is provide a reduced-oxygen breathing device for providing oxygen-reduced/ nitrogen-enriched air to a subject and connected to an aircraft flight simulator to provide hypoxia training.

A still further object of the invention is to provide a reduced-oxygen breathing device for providing oxygen-reduced/nitrogen-enriched air to a subject and connected to a treadmill to provide a stress EKG test.

An additional object of this invention is to provide a reduced-oxygen breathing device for providing oxygen-reduced/nitrogen-enriched air to a subject having reduced lung capacity to evaluate the person's fitness for an aircraft flight or travel to a high-altitude location.

These and other objects, features and advantages of the present invention are described in or are apparent from the following detailed description of preferred embodiments.

BRIEF DESCRIPTION OF THE DRAWINGS

The invention will be described with reference to the drawings, in which like elements have been denoted throughout by like reference numerals. The representation in each of the figures is diagrammatic and no attempt is made to indicate actual scales or precise ratios. Proportional relationships are shown as approximations.

FIG. 6 shows an alveolar gas table for oxygen concentrations of air at various altitudes and an algorithm for calculating the same.

DETAILED DESCRIPTION OF THE PREFERRED EMBODIMENT

Figure 1:
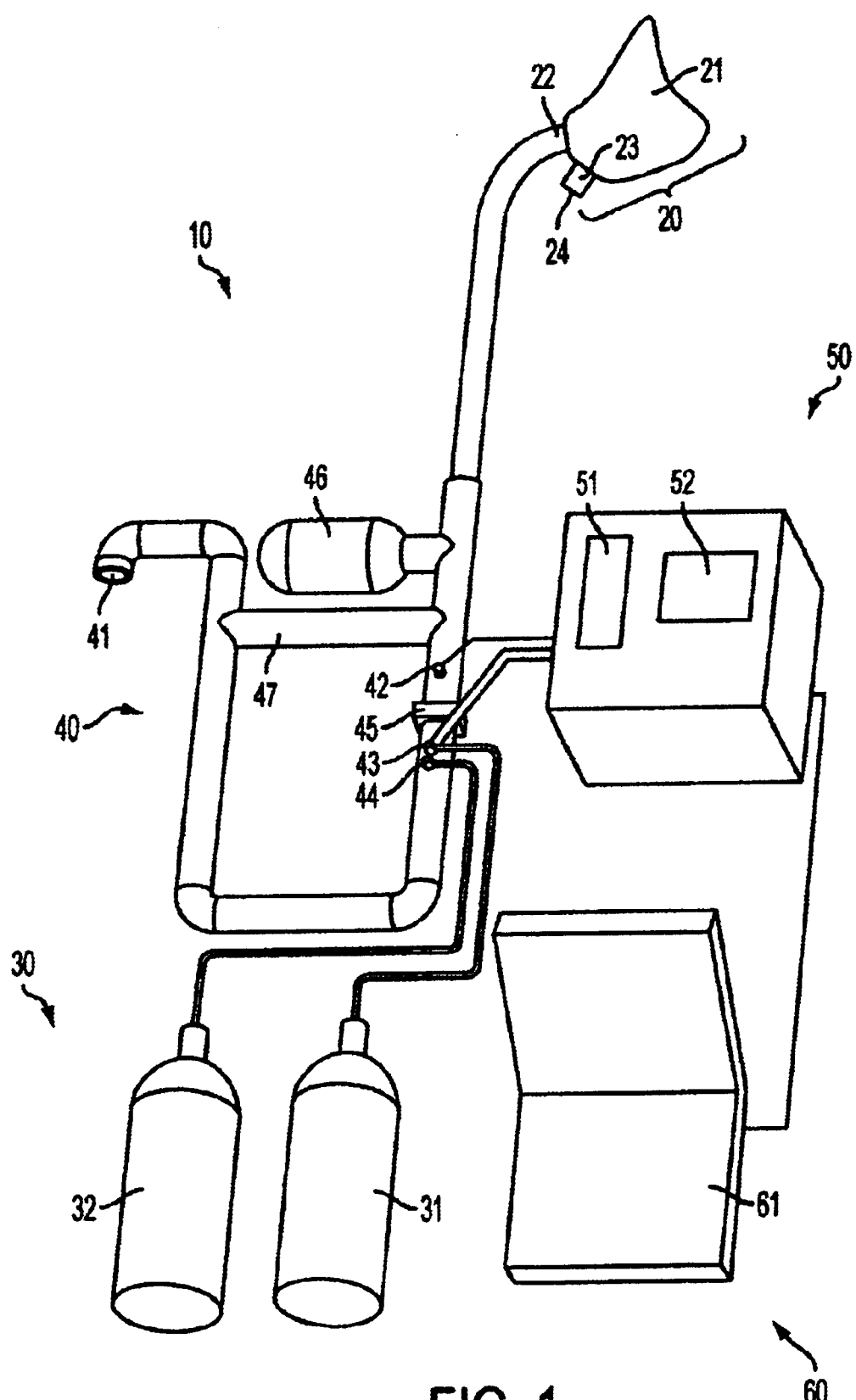
FIG. 1 shows a reduced-oxygen breathing device for providing oxygen-reduced/nitrogen-enriched air to a subject.

The Reduced-Oxygen Breathing Device (ROBD) is designed to create a predetermined static or dynamic gas mixture that can be used for breathing and is intended to induce hypoxia in a subject. The reduced-oxygen breathing apparatus is made up of the following minimum elements:

(a) Vessel for Gas Mixing. In the preferred embodiment, this vessel consists of a hollow loop of polyvinyl chloride piping within which the mixing of the gases occurs. However, the vessel can be of any configuration (sphere, oval, straight pipe, etc.) that is suitable to allow the mixing of gases. Nitrogen is added to the vessel and dilutes the ambient air so that an operator-selected concentration of oxygen is obtained within the loop and is available for breathing by the subject. In an alternative embodiment, oxygen can also be added to the vessel to aid in controlling the concentration of oxygen within the loop or to bring pure oxygen to the subject in case of emergency or as required by the study being conducted.

(b) Ambient Air Inlet. This inlet allows air the external (ambient) environment to be introduced into the vessel. In the preferred embodiment, the inlet consists of a one-way valve opening from the ambient environment into the loop. This inlet valve is in fluid communication with the gas mixing vessel to allow the flow of air from the ambient environment to the vessel.

(c) Outlet. This outlet allows the controlled gas mixture to exit the vessel and be introduced to the subject. In the preferred embodiment, the valve consists of a one-way valve in fluid communication with the loop and is operatively connected to a delivery unit. This delivery unit may be a face-mask having a one-way valve opening towards the subject who breathes the controlled gas mixture and exhales through another one-way valve opening to the ambient environment. The facemask can be a standard aviator's oxygen mask to make flight-testing more realistic.

(d) Oxygen Concentration Sensor. This sensor allows for frequent sampling of the gas mixture within the vessel. The sensor may measure oxygen directly or it may be a nitrogen (or other gas) sensor from which the concentration of oxygen can be extrapolated. In the preferred embodiment, the oxygen content of the gas mixture oxygen is measured directly. The output of this oxygen sensor is a voltage, which is directly proportional to the concentration of oxygen in the mixture. This voltage is fed into a commercially available data acquisition card, and utilized as input values for a customized software program (LabView, Inc.).

(e) Nitrogen Gas Supply. Nitrogen gas from a compressed-gas cylinder is supplied through a valve to the gas mixing vessel. The valve is actuated by an output signal from the controller (see below) thereby regulating the flow of nitrogen gas to the gas mixing vessel.

(f) Controller for Gas Mixing. The controller provides a means by which the operator can precisely control the gas mixture (oxygen content) within the vessel and is accomplished by use of data acquisition card to receive data from the oxygen sensor and a computer with customized software that calculates the amount of nitrogen (if any) that must be introduced into the vessel to obtain the selected concentration of oxygen. The software was modified from commercially available software (LabView, Inc.) to accomplish the tasks shown in the decisional block diagram of FIG. 5. One skilled in the art of computer programming will appreciate that various algorithms can be employed to obtain this software functionality. As the gas mixture within the vessel passes over an oxygen concentration sensor, the oxygen content of the gas mixture is measured. The voltage output of the sensor is directly proportional to the concentration of oxygen in the mixture. This voltage output is reported into a commercially available data acquisition card, and utilized as input values for a purpose-built software program. This software control monitors the concentration of oxygen in the mixing loop (expressed as voltage and converted to percent oxygen) and continuously compares this value to a value that has been selected by the device operator. In sum, the oxygen concentration sensor sends a signal to the controller (data acquisition card and computer equipped with customized software) which manipulates the signal and then provides an output signal to the nitrogen valve that adjusts the nitrogen gas supply to the gas mixing vessel In the preferred embodiment of the ROBD, mixing of the gases occurs in a loop of polyvinyl chloride (PVC) pipe that has a one-way valve opening to ambient air on one end, and is connected to a delivery system to the subject on the other end. Note that any suitable airtight material, i.e., PVC tubing, stainless steel or aluminum tubing, may be employed to construct the vessel. An elastic reservoir (a bladder) is connected in series with the mixing loop which serves to modulate the pressure and volume changes in the loop as a result of gas fluctuations. A computer runs a custom software program to control the relative percentages of oxygen and nitrogen in the loop. The control of the gas mixture is achieved through a feedback loop between the mixing circuit and computer-controlled solenoid valves connected to external supplies of nitrogen and oxygen. Finally, a power source is required for the multiple solenoid valves and one or more mixing fans.

Figure 5:
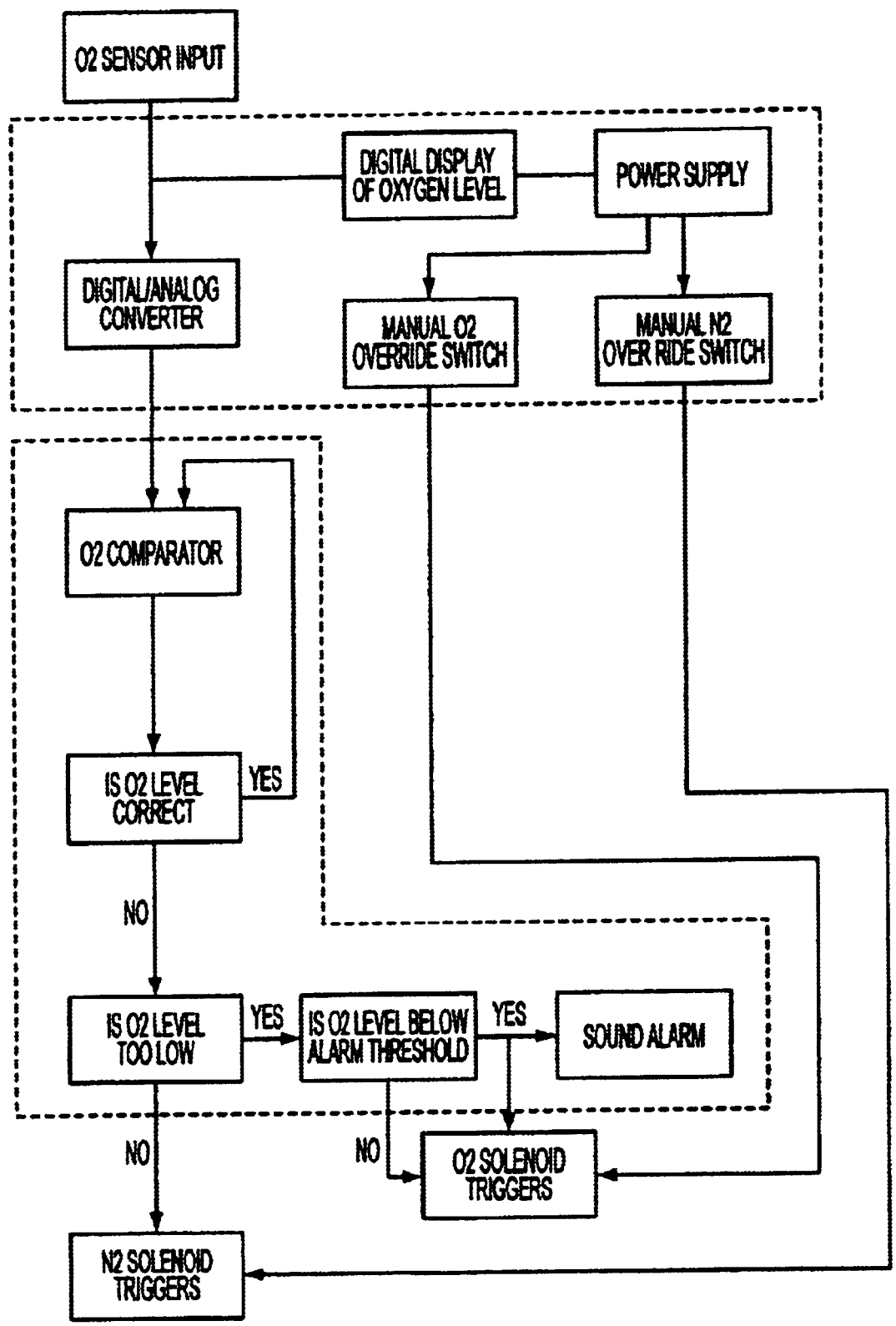
FIG. 5 shows a decisional block diagram of hardware and software interactions according to a preferred embodiment of a reduced-oxygen breathing device for providing oxygen-reduced/nitrogen-enriched air to a subject.

Ambient air is drawn into the mixing loop by the respirations of the subject. This gas mixture passes over an oxygen sensor, which reads the oxygen content of the gas mixture. The output of this sensor is a voltage, which is directly proportional to the concentration of oxygen in the mixture. This voltage is fed into a commercially available data acquisition card, and utilized as input values for a customized software program. FIG. 5 shows a schematic of hardware and software interactions according to a preferred embodiment of a reduced-oxygen breathing device for providing oxygen-reduced/nitrogen-enriched air to a subject.

The data acquisition card, as used in the present invention, is an automation device which serves as an interface between the sensor and the computer. The data acquisition card reads the output of the sensor (voltage) and provides for the conversion from an analog signal to a digital signal for use by the customized computer program. Essentially, this data acquisition card serves as an interface between computers and the physical world: it reads the output of sensor(s) and brings this data into a PC where it can be stored and processed by the software as desired. This software control monitors the concentration of oxygen in the mixing loop (expressed as voltage and converted to percent oxygen) and continuously compares this value to a value that has been selected by the device operator. The set point value can be obtained in several ways.

One approach is that the operator can choose a fixed concentration of oxygen to be administered. If the actual concentration of oxygen in the mixing loop exceeds the expected value, nitrogen is injected into the mixing loop until the actual concentration and expected concentrations match. In an alternative embodiment, if the actual oxygen concentration of oxygen in the mixing loop is less than the expected oxygen concentration, oxygen can be injected into the system until the actual and expected values match. Actual and expected concentrations are compared at an operator-selectable frequency. Adjustments to the gas mixture are made by way of software driven solenoid valves connected to the cylinders of nitrogen and oxygen.

In another approach, the device can be programmed to present variable concentrations of oxygen as a function of time, thereby creating a state in which the subject is presented with different gas mixtures at different times. Since the ROBD continuously compares expected oxygen concentration with observed concentration, each breath can contain a slightly different percentage of oxygen, if so desired by the experimenter. The data from the device is written to files on the control computer. This feature enables later analysis of the actual oxygen concentrations delivered to the subject, and can be correlated with physiologic measurements, or with performance on particular tasks.

The present invention addresses the shortcomings noted in the prior art (see Background Section above) by using a non-rebreathing circuit coupled with computer-controlled gas adjustments. Ambient air is diluted with nitrogen on a breath-by-breath basis, providing the experimenter with precise control over the inspired concentration of oxygen on an almost instantaneous basis. Carbon dioxide and water vapor exhaled by the subject are released into the environment, and absorption is not necessary. In addition, the mixed gas can be administered through a standard aviator's oxygen mask, increasing the realism of the simulation and removing obvious external cues on the nature of the experiment. The ROBD, as configured, attaches to a standard aviator's oxygen mask. The small size of the present invention makes fitting the device into cramped simulator environments possible, and multiple units may be incorporated into multi-place aircraft simulators. Maintenance on the mixing loop is low when compared to re-breathing units, since no consumable items are necessary to absorb water vapor and/or carbon dioxide.

According to the preferred embodiment, the mixing and homogenizing loop is made of 3" schedule 40 PVC, having a volume of approximately 500 cubic inches. Preferably, the continuous mixing loop within the system has a minimum volume of 500 cubic inches. The inventors have also built a smaller, alternate embodiment using 1½" PVC tubing and having a volume of approximately 150 cubic inches. This volume was found to be marginal as a well-conditioned athlete could consume the air within the system that simulated high altitude (i.e., 25,000 feet) as fast as the device could create the simulated air. The alternate embodiment is operative. However, in the alternate embodiment it is difficult for the control system to maintain the correct concentrations of gases for simulated air at the desired altitude.

According to the preferred embodiment, the ROBD also includes a mixing fan. The mixing loop volume and the fan flow rate are configured to provide a re-circulation rate per unit volume of air of at least one time per second. According to the preferred embodiment, the fan supplies a flow rate of 45 cubic feet per minute (cfm). According to the alternate embodiment, a fan with a flow rate of 21 cfm is utilized. The fans were sized to deliver minimum flow rates that allow the air in the continuous loop portion of the system to re-circulate at least 2.5 times per second, preferably 4 cycles per second. The device volume and fan flow rate provides an invention that delivers simulated altitude air with a very homogenous mixture of oxygen and nitrogen.

According to the preferred embodiment, the power supply that provides power to the DC mixing fan is a 110 volt A/C input with a 12 volt DC output of at least 200 mA. The inventors have configured a portable embodiment that runs off a 12-volt DC battery. According to the preferred embodiment, the inflatable bladder has a total volume when fully expanded of 30 cubic inches. This bladder typically inflates only approximately 20%. Therefore the actual volume needed by the bladder is only about 6 cubic inches in the preferred embodiment. For a device with a larger or smaller volume, the inflatable bladder will be sized to be larger or smaller, respectively, to remain consistent with that volume size.

A working scheme of the preferred embodiment of the reduced-oxygen breathing device 10 is shown in FIG. 1. This preferred embodiment consists of an open loop 40 ROBD, the loop being made from PVC tubing 47, but any suitable material would suffice. At one end 20 of the ROBD, the subject is delivered the selected concentration of oxygen through a delivery unit 22, preferably a flexible hose. As the subject inhales air through a face-mask 21 connected to the delivery tube 22, replacement room (ambient) air enters the embodiment thru a one-way valve or flapper valve 41. An outlet 23 on the face-mask 20 having a one-way valve or flapper valve 24 prevents the subject's exhaled air from entering the reduced-oxygen breathing device. The oxygen level within the embodiment is measured with an oxygen sensor or nitrogen sensor or dual sensors for oxygen and nitrogen 42, which determines the amount of oxygen in the air being delivered to a subject for inhalation. The voltage output of this sensor is fed into an interface device 50 which links the ROBD to a microprocessor 60. The interface device 50 contains a data acquisition card which reads the output of the sensor (voltage) and provides for the conversion from analog to digital (and back) for use by software in the computer program of the microprocessor 60. The digital output from the data acquisition card is compared to the desired level of oxygen with a laptop computer or other digital microprocessor 60 and an electronic comparator, look-up table, or other suitable algorithm. An electronic solenoid for both oxygen 43 and nitrogen 44 are utilized by the electronics to adjust the level of oxygen to the desired level. A readout of the actual oxygen 52 or nitrogen 51 concentration is provided on the interface device 50. The system may be operated in one mode by obtaining the desired oxygen content solely by adjusting (via software) the nitrogen gas levels fed into the ROBD system (via the interface device). An alternate manner of operation is to adjust both the oxygen and nitrogen levels fed into the system. Because the ambient air will have concentrations of oxygen higher than those desired during normal operation of this system (e.g., levels designed to induce hypoxia in the subject), the former mode (using nitrogen to displace the oxygen) is simpler and more preferred. The operator may preset or change the desired oxygen concentrations by communication with the software program via the computer keyboard 61. The stored oxygen and nitrogen 30 are located in compressed bottles 31 and 32, respectively. A mixing fan 45 is employed to provide a homogenous mixture for a more accurate measurement. An inflatable bladder 46 is utilized for slight variations of pressure in the preferred embodiment while the subject is breathing.

Figure 2:
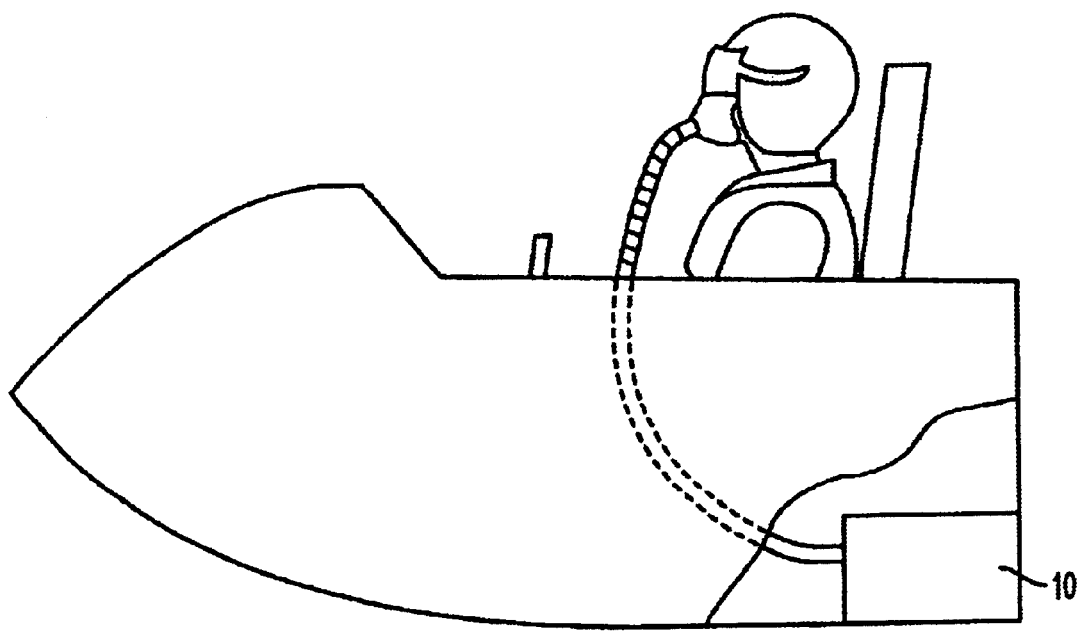
FIG. 2 shows a reduced-oxygen breathing device for providing oxygen-reduced/nitrogen-enriched air to a subject and connected to an aircraft flight simulator to provide hypoxia training.
Figure 3:
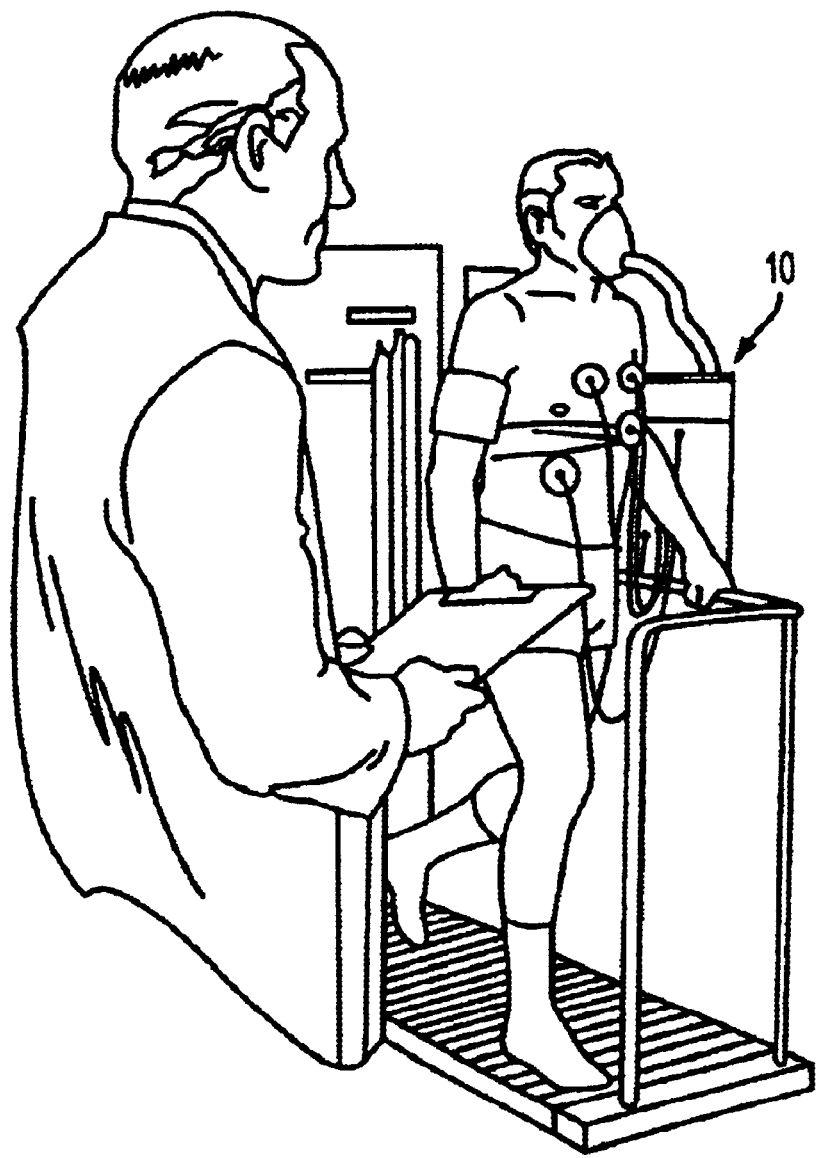
FIG. 3 shows a reduced-oxygen breathing device for providing oxygen-reduced/nitrogen-enriched air to a subject and connected to a treadmill to provide a stress EKG test.
Figure 4:
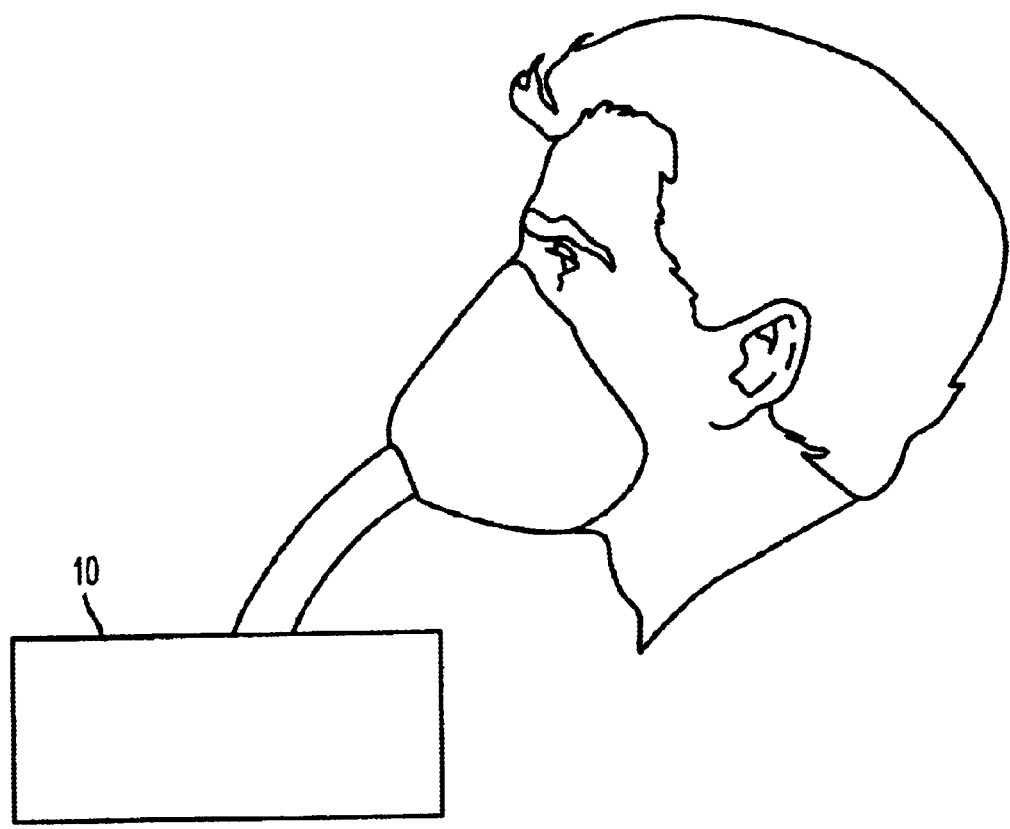
FIG. 4 shows a reduced-oxygen breathing device for providing oxygen-reduced/nitrogen-enriched air to a subject having a lowered lung capacity to evaluate that person's fitness for an aircraft flight or travel to a high-altitude location.

FIGS. 2–4 show a depiction of some of the contemplated applications for the ROBD. FIG. 2 shows a ROBD for providing oxygen-reduced air to a subject and connected to an aircraft flight simulator to provide hypoxia training. FIG. 3 shows a reduced-oxygen breathing device for providing oxygen-reduced air to a subject and connected to a treadmill to provide a stress EKG test. FIG. 4 shows a reduced-oxygen breathing device for providing oxygen-reduced air to a subject having a lowered lung capacity to evaluate that person's fitness for an aircraft flight or travel to a high-altitude location.

FIG. 5 shows a decisional block diagram of hardware and software interactions according to a preferred embodiment of a reduced-oxygen breathing device for providing oxygen-reduced/nitrogen-enriched air to a subject. The top box (dashed lines) shows the processes that take place in the interface device and are accomplished by the data acquisition card of that device. The lower box shows the steps that are accomplished by software within the microprocessor (a laptop in the preferred embodiment).

FIG. 6 shows an alveolar gas table for oxygen concentrations in air at various altitudes and a representative algorithm for calculating the same.

Figure 7:
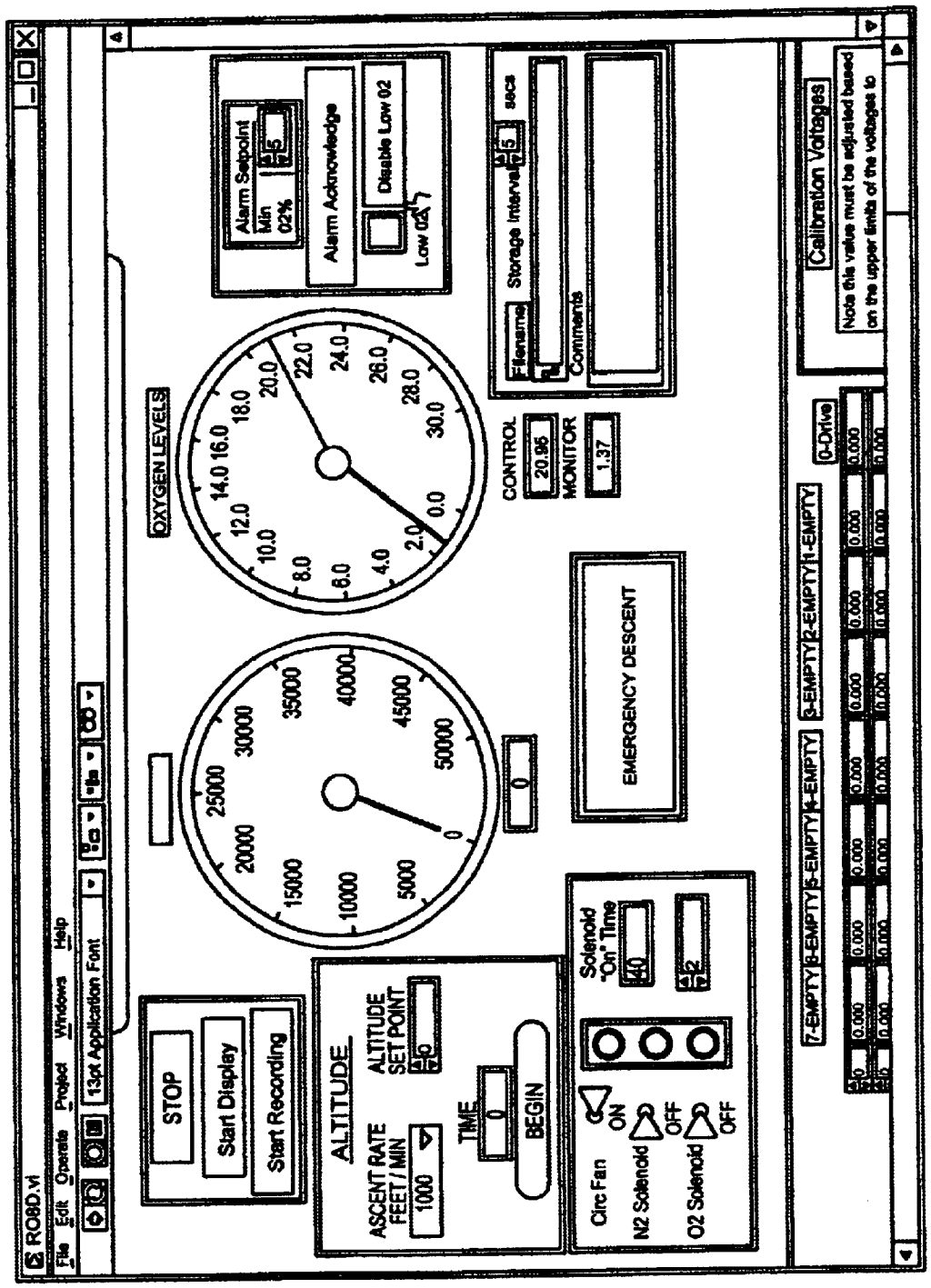
FIG. 7 shows a screen display of various aspects of a preferred embodiment of a reduced-oxygen breathing device for providing oxygen-reduced and nitrogen-enriched air to a subject.

FIG. 7 shows a computer screen display of various aspects of a preferred embodiment of a reduced-oxygen breathing device for providing oxygen-reduced and nitrogen-enriched air to a subject. Program start and stop controls along with a recording feature are displayed in the upper left-hand corner. Below that, the altitude control settings are shown with accent rate function and time settings. Altitude can be static where a steady altitude can be maintained, or it may be dynamic where an ascent (and descent) over time can be simulated. Directly below the altitude feature are the switches for the fan, nitrogen solenoid, and oxygen solenoid (if present), as well as 'on-time' displays for the solenoids. The left circular display shows the actual altitude and the right displays the actual percent oxygen. The box directly below these circular displays shows the 'emergency descent' feature in which oxygen is fed into the system at a high rate to bring the subject back (if necessary) from hypoxic conditions. The box directly to the right of the circular displays shows the alarm feature. The operator can set lower limit parameters for oxygen content, and if the setting is surpassed, the alarm will be activated. The file may be named and test comments recorded for future reference.

The inventors contemplate the following applications for the present invention:

1. For use in conjunction with an aircraft simulator
2. For use as a stress EKG test
3. For use in cardio training with a reduced level of exercise required
4. For use in altitude conditioning
5. For use in evaluating a person that has reduced lung capacity and will be exposed to reduced oxygen content (flying)

In summary, the present invention includes a non-rebreathing circuit coupled with computer-controlled gas adjustments. Ambient air is diluted with nitrogen on a breath-by-breath basis, providing the experimenter with precise control over the inspired concentration of oxygen/nitrogen mixture on an almost instantaneous basis. Carbon dioxide and water vapor exhaled by the subject are released into the environment, and absorption is not necessary. In addition, the mixed gas can be administered through a standard aviator's oxygen mask, increasing the realism of the simulation and removing obvious external cues on the nature of the experiment. The ROBD as configured attaches to a standard aviator's oxygen mask, which enables the use of personal equipment for administration of the gas mixture. The small size of the present invention makes fitting the device into cramped simulator environments possible, and multiple units may be incorporated into multi-place aircraft simulators. Maintenance on the mixing loop is lower compared to re-breathing units, since no consumable items are necessary to absorb water vapor and/or carbon dioxide. The inventors further contemplate uses of invention such that the 'subject' for the device may be any mammal, including a cat, dog, horse, pig, non-human primate, or human. It is within the skill in the art to configure the mask for the selected mammal. The device may fit inside a portable housing, such as a hermetically-sealed suitcase for convenient storage and shipping.

Obviously, many modifications and variations of the present invention are possible in light of the above teachings. It is therefore to be understood that, within the scope of the appended claims, the invention may be practiced otherwise than as specifically described.

We claim:

1. A reduced-oxygen breathing apparatus comprising:
   (h) a vessel for gas mixing, wherein said gas mixing vessel is a hollow loop;
   (i) an ambient air inlet, said inlet being in fluid communication with said gas mixing vessel;
   (j) an outlet, said outlet being in fluid communication with said gas mixing vessel on one end and providing a controlled gas mixture to a subject at the opposite end;
   (k) an oxygen concentration sensor, said sensor being in fluid communication with the gas mixing vessel;
   (l) a nitrogen gas supply, said nitrogen gas supply being in fluid communication with said gas mixing vessel;
   (m) a nitrogen valve in fluid communication with said gas mixing vessel and said nitrogen gas supply, wherein said nitrogen valve controls flow of said nitrogen gas supply to said gas mixing vessel; and
   (n) a controller for said gas mixing, wherein:
      said oxygen concentration sensor sends a signal to said controller;
      said controller manipulates said signal;
      said controller provides an output signal to said nitrogen valve that adjusts said nitrogen gas supply to said gas mixing vessel in accordance with parameters set by an operator; and
   further comprising a nitrogen concentration sensor in fluid communication with said loop.

2. The reduced-oxygen breathing device of claim 1, wherein said ambient air inlet has a one-way valve in fluid communication with said inlet, said valve providing introduction of ambient air into said loop.

3. The reduced-oxygen breathing device of claim 2, wherein said outlet is in fluid communication with said loop and is operatively connected to a delivery unit providing said controlled gas mixture to said subject.

4. The reduced oxygen breathing device of claim 3, wherein said delivery unit is a face-mask having:
   a one-way valve in fluid communication with said loop and opening towards said subject, and
   a one way valve opening to the ambient environment for exhalation of said controlled gas mixture by said subject.

5. The reduced oxygen breathing device of claim 4, wherein said face-mask is a standard aviator's oxygen mask.

6. The reduced-oxygen breathing device of claim 1, further comprising an oxygen gas supply, said oxygen gas supply being in fluid communication with said loop.

7. The reduced-oxygen breathing device of claim 6, further comprising an oxygen valve in fluid communication with said gas mixing vessel and said oxygen gas supply, wherein said oxygen valve controls flow of said oxygen gas supply to said gas mixing vessel.

8. The reduced-oxygen breathing device of claim 1, further comprising a mixing fan in fluid communication with said loop and is connected to a power source.

9. The reduced-oxygen breathing device of claim 8, wherein said mixing fan supplies a flow rate of between 10 and 100 cubic feet per minute.

10. The reduced-oxygen breathing device of claim 8, wherein said mixing fan supplies a flow rate of between 20 and 45 cubic feet per minute.

11. The reduced-oxygen breathing device of claim 1, wherein said loop is composed of 3" PVC tubing and has a minimum volume of about 500 cubic inches.

12. The reduced-oxygen breathing device of claim 1, wherein said loop is composed of 1½" PVC tubing and has a volume of about 150 cubic inches.

13. The reduced-oxygen breathing device of claim 1, further comprising an electrical power source connected to said sensor, controller, and said valve, and wherein said controller is electrically connected with said oxygen concentration sensor and said solenoid.

14. The reduced-oxygen breathing device of claim 13, wherein said controller comprises a data acquisition card connected to a laptop computer.

15. The reduced-oxygen breathing device of claim 14, wherein said oxygen concentration sensor provides a voltage input to said data acquisition card, said voltage is converted to a digital signal by said data acquisition card, said digital signal is compared to the desired level of oxygen by said laptop computer and an electronic comparator, and said controller sends said output signal to said nitrogen valve based on the result of said comparison.

16. The reduced-oxygen breathing device of claim 14, wherein said oxygen concentration sensor provides a voltage input to said data acquisition card, said voltage is converted to a digital signal by said data acquisition card, said digital signal is compared to the desired level of oxygen by said laptop computer and an algorithm, and said controller sends said output signal to said nitrogen valve based on the result of said comparison.

17. The reduced-oxygen breathing device of claim 1, further comprising an inflatable bladder in fluid communication with said loop.

18. The reduced-oxygen breathing device of claim 1, wherein said controller is programmed to present variable concentrations of oxygen as a function of time.

19. The reduced-oxygen breathing device of claim 1, wherein said nitrogen valve is a nitrogen solenoid.

20. The reduced-oxygen breathing device of claim 1, wherein said signal is an electrical signal.

* * * * *